United States Patent [19]
Momose et al.

[11] Patent Number: 5,365,439
[45] Date of Patent: Nov. 15, 1994

[54] METHOD AND APPARATUS FOR DETECTING FRICTION COEFFICIENT OF ROAD SURFACE, AND METHOD AND SYSTEM FOR FOUR-WHEEL STEERING OF VEHICLES USING THE DETECTED FRICTION COEFFICIENT OF ROAD SURFACE

[75] Inventors: Nobuo Momose; Hiroaki Yoshida, both of Okazaki, Japan

[73] Assignee: Mitsubishi Jidosha Kogyo Kabushiki Kaisha, Tokyo, Japan

[21] Appl. No.: 727,232

[22] Filed: Jul. 5, 1991

[30] Foreign Application Priority Data

Jul. 6, 1990 [JP] Japan .................................. 2-179239

[51] Int. Cl.⁵ ......................... B62D 7/15; G06F 15/48
[52] U.S. Cl. ..................... 364/424.05; 364/426.01; 364/424.01; 180/140; 180/142
[58] Field of Search ............... 364/424.05, 425, 424.01, 364/424.04, 424, 426.01, 426.03; 180/140, 141, 142, 197; 303/100

[56] References Cited

U.S. PATENT DOCUMENTS

| | | | |
|---|---|---|---|
| 4,140,440 | 2/1979 | Ferris | 417/343 |
| 4,718,514 | 1/1988 | Hirakushi | 180/142 |
| 4,721,176 | 1/1988 | Kabasin et al. | 180/197 |
| 4,834,205 | 5/1989 | Mizuno et al. | 180/141 |
| 4,836,319 | 6/1989 | Haseda et al. | 180/142 |
| 4,848,851 | 7/1989 | Kuraoka et al. | 303/100 |
| 4,875,542 | 10/1989 | Uchida et al. | 180/142 |
| 4,882,693 | 11/1989 | Yopp | 364/424.01 |
| 4,940,103 | 7/1990 | Moniyama | 180/132 |
| 4,964,481 | 10/1990 | Sano et al. | 180/140 |
| 5,075,854 | 12/1991 | Imaseki et al. | 304/424.05 |
| 5,147,008 | 9/1992 | Nishimore et al. | 180/140 |

FOREIGN PATENT DOCUMENTS

| | | |
|---|---|---|
| 2558130 | 7/1985 | France . |
| 3409040 | 9/1985 | Germany . |
| 8802483 | 4/1988 | Germany . |
| 2105776 | 5/1987 | Japan . |

Primary Examiner—Thomas G. Black
Assistant Examiner—Jacques Harold Louis-Jacques

[57] ABSTRACT

A method for detecting a friction coefficient of the road surface includes a detection step of detecting an operating angle of the steering wheel of the vehicle, a vehicle speed and an operating pressure of the hydraulic power steering unit for the front wheels, and a calculation step of calculating the friction coefficient of the road surface on turning of the vehicle by considering relationships among a slip angle of the front wheel, the friction coefficient of the road surface and a cornering force of the front wheels. The method further includes a step of prohibiting the execution of the calculation step when the steering wheel is turned back, whereby the calculation step is executed only when the direction of the operating pressure of power steering unit is in the equiphase with the operating direction of the steering wheel. Also, a four-wheel steering system includes has a rear steering actuator for steering the rear wheels so as to increase the steering angle of the rear wheels as the friction coefficient of the road surface calculated by the above-described method decreases.

18 Claims, 10 Drawing Sheets

METHOD AND APPARATUS FOR DETECTING FRICTION COEFFICIENT OF ROAD SURFACE, AND METHOD AND SYSTEM FOR FOUR-WHEEL STEERING OF VEHICLES USING THE DETECTED FRICTION COEFFICIENT OF ROAD SURFACE

BACKGROUND OF THE INVENTION

1. Field of the Invention

Firstly, the preset invention relates to a method and an apparatus for determining the ease of slip on road surfaces on running vehicles, that is, for detecting the friction coefficient of road surface. Secondly, the present invention relates to a method and a system for four-wheel steering of vehicles in which the steering of rear wheels is controlled by using the detected friction coefficient of road surface, when the front wheels of vehicle are steered.

2. Description of the Related Art

The method for detecting the friction coefficient of road surface and the method for four-wheel steering of vehicles have been disclosed, for example, in Unexamined Japanese Patent Publication No. 60-148769 (U.S. Pat. No. 4,964,481, DE 3,500,797, GB 2,153,311, FR 2,558,130). According to the former method of these two known methods, the friction coefficient of road surface is detected on the basis of the operating angle of steering wheel of vehicle, the vehicle speed, and the lateral acceleration acting on the vehicle body. According to the latter method, the steering angle of rear wheels on vehicle is corrected in accordance with the friction coefficient of road surface detected by the former method.

The above-described method for detecting the friction coefficient of road surface will be explained below in more detail. First, the slip angle of the front wheel is calculated from the operating angle of steering wheel and the vehicle speed. The slip angle correlates with the cornering force of front wheel, and the cornering force varies with the friction coefficient of road surface. Meanwhile, it is well known that the cornering force is proportional to the lateral acceleration acting on the vehicle body. If the operating angle, the vehicle speed, and the lateral acceleration are detected, therefore, the friction coefficient of road surface can be calculated on the basis of the detection results.

The lateral acceleration which the vehicle body is to be subjected during the turning of vehicle actually acts on the body only when some time elapses after the start of turning. Since the lateral acceleration acts on the vehicle body subsequent to a delay after the start of turning of the vehicle, there is a delay in detecting the lateral acceleration of vehicle body. For this reason, the friction coefficient of road surface cannot be calculated quickly by the above-described method.

The cornering force calculated from the lateral acceleration acting on the vehicle body is equivalent to the sum of the cornering forces generated on the front and rear wheels. When the friction coefficient of road surface is calculated on the basis of the cornering force obtained from the lateral acceleration, therefore, the slip angle of not only the front wheels but also the rear wheels should be taken into consideration. With the conventional method, in which the slip angle of front wheels only is taken into consideration, the friction coefficient of road surface cannot be exactly detected, resulting in poor accuracy of the detected friction coefficient of road surface.

SUMMARY OF THE INVENTION

The first object of the present invention is to provide a method and an apparatus for quickly and accurately detecting a friction coefficient of the road surface at the initial turning stage of vehicle. The second object of the present invention is to provide a method and a system for four-wheel steering of vehicle in which the steering control of rear wheels can be performed in an optimum manner when the front wheels are steered.

The first object can be achieved by the method and apparatus for detecting a friction coefficient of the road surface according to the present invention, the method comprising:
 a first step of detecting each of an operating angle of the steering wheel of the vehicle, a speed of vehicle and an operating pressure of a hydraulic power steering unit for the front wheels of vehicle,
 a second step of detecting a proper steering situation in which a condition of increase in the operating angle of front wheels is satisfied during the operation of steering wheel, and
 a third step of calculating a friction coefficient of the road surface on the basis of the data detected in the first step only when the proper steering situation is detected.

In the third step, the friction coefficient of road surface is calculated by using relationships of three conditions: firstly, a slip angle of front wheels is determined in accordance with the operating angle of steering wheel, the vehicle speed, and the friction coefficient of road surface, secondly, a cornering force of front wheels is determined in accordance with the slip angle and the friction coefficient of road surface; and thirdly, the cornering force is proportional to the operating pressure of power steering unit.

With the above-described method, in which the operating pressure of hydraulic power steering unit is used as a factor in proportion to the cornering force, the friction coefficient of road surface can be exactly detected. The detecting accuracy is increased by taking account of the operating pressure corresponding to the cornering force of front wheels only.

The operating pressure of hydraulic power steering unit is generated quickly at the initial turning stage of vehicle, in other words, at the start of operation of steering wheel. Thus, the friction coefficient of road surface can be exactly detected even at the initial turning stage of vehicle.

Even though the operating angle of steering wheel is equal, the increasing and decreasing characteristics of operating pressure of hydraulic power steering unit differs greatly between the turning and turning back operations of steering wheel. For this reason, if the friction coefficient of a road surface is calculated at all times when the steering wheel is operated, a large error may be produced in the detected friction coefficient of road surface. According to the present invention, the friction coefficient of road surface is calculated only when the operating angle of steering wheel increases or is held at a predetermined angular position during the operation of steering wheel. Thus, a stable and reliable friction coefficient of surface road can be calculated.

Preferably, the detected signal indicating the operating pressure of the power steering unit may be filtered to compensate the advance in phase of operating pressure in relation to the operation of steering wheel. The advance in phase of operating pressure is caused by the characteristics of a steering valve in the power steering unit and the inertia effect of front wheels. The filtering of the detected signal or the operating pressure further increases the detection accuracy of friction coefficient of road surface.

The operating pressure of a hydraulic power steering unit is preferably detected as the pressure difference between right and left pressure chambers in the power steering unit. If the operating pressure of power steering unit is detected in such a manner, a discrimination can be made as to whether or not the condition of the second step described above has been satisfied, that is, whether or not the proper steering situation has been detected. This is by taking account a steering direction of the front wheels corresponding to the acting direction of operating pressure and a steering direction of the front wheels corresponding to the operating angle of steering wheel.

Since the friction coefficient of road surface in the third step is calculated only when the proper steering situation is detected, the friction coefficient, of road surface is not calculated, for example, when the vehicle is slaloming and the steering phases determined on the basis of the operating pressure and the operating angle of steering wheel are opposite. As a result, there is no error in friction coefficient of road surface, and the detection accuracy is further increased.

When the absolute value of change ratio of the calculated friction coefficient of road surface is higher than a predetermined value, it is desirable that the calculated friction coefficient of road surface should not be set as a new friction coefficient. This prevents a sudden change of the detected friction coefficient of road surface, thus providing a stable friction coefficient of road surface.

The apparatus for detecting a friction coefficient of the road surface is an apparatus for carrying out the above-described method. The apparatus has advantages similar to those of the detecting method.

The second object of the present invention described above is achieved by a four-wheel steering method of vehicle according to the present invention, the four-wheel steering method comprising:

- a first step of detecting each of an operating angle of the steering wheel, a vehicle speed and an operating pressure of a hydraulic power steering unit for the front wheels,
- a second step of detecting a proper steering situation in which a condition of increase in the steering angle of front wheels is satisfied during the operating of steering wheel,
- a third step of calculating a friction coefficient of the road surface on the basis of the data detected in the first step only when the proper steering situation is detected, and
- a fourth step of calculating an equiphase steering angle of rear wheels to steer the rear wheels to the same direction as the steering direction of front wheels, on the basis of the rotating angle of steering wheel and the friction coefficient of road surface obtained in the third step, the equiphase steering angle of rear wheels calculated in the fourth step being increased by a predetermined increment as the friction coefficient of road surface calculated in the third step decreases.

With the above-described four-wheel steering method, the friction coefficient of road surface can be detected accurately at the initial turning stage of vehicle, as with the above-described detecting method. Thus, the optimum equiphase steering angle of rear wheels can be calculated on the basis of the friction coefficient of road surface thus detected.

With the four-wheel steering method according to the present invention, the turning ability of vehicle can be fully insured even when the friction coefficient of road surface is low, since the equiphase steering angle of rear wheels is increased with the decrease in friction coefficient of road surface.

The increase in equiphase steering angle of rear wheels caused by a low friction coefficient of road surface should be preferably restricted with the increase in vehicle speed. This restriction permits the optimum correction of equiphase steering angle of rear wheels in accordance with the decrease in friction coefficient of road surface when the vehicle is running at either a medium or a high speed, resulting in higher steering stability of the vehicle.

It is also preferable to calculate the steering angle of rear wheels by taking into account an opposite phase steering angle for steering the rear wheels in the direction opposite to the steering of front wheels in addition to the equiphase steering angle described above. This opposite phase steering angle is calculated in accordance with the angular velocity of the steering wheel. In calculating the opposite please steering angle, it is desirable that the opposite phase steering angle be increased as the friction coefficient of the road surface decreases. If the opposite phase steering angle is calculated in this way, the turning ability of the vehicle front is further improved during the turning of the vehicle even when the road surface has a low friction coefficient.

The four-wheel steering system of the vehicle is a system for implementing the above-described steering method, and has advantages similar to those of the four-wheel steering method.

Other features and objects of the present invention will become more apparent from the following description of the preferred embodiments with reference to accompanying drawings.

DETAILED DESCRIPTION OF THE PREFERRED EMBODIMENTS

Figure 1:
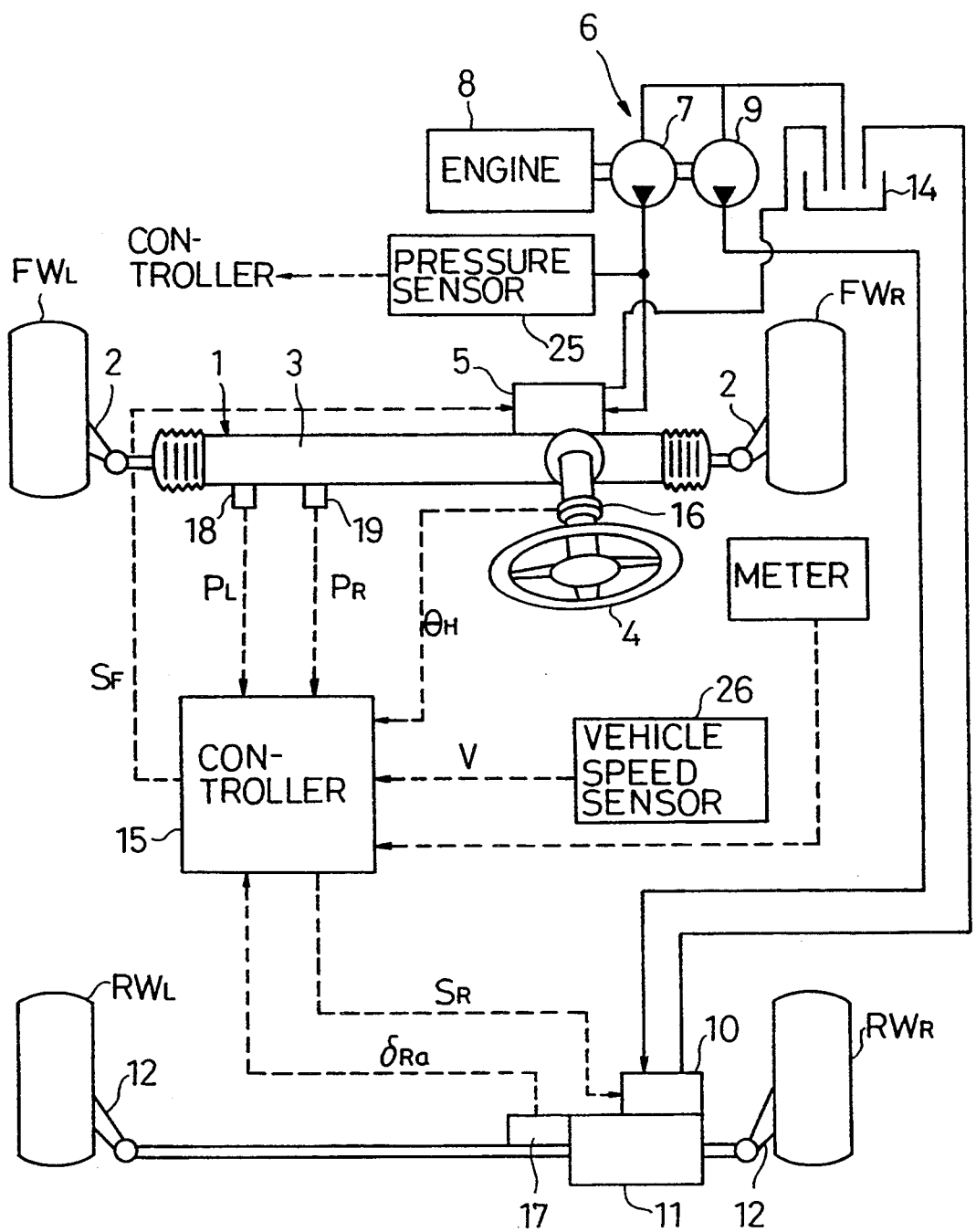
FIG. 1 is a schematic view of a four-wheel steering system according to the present invention.

Referring to FIG. 1, which schematically shows a four-wheel steering system of vehicle, the left front, wheel $FW_L$ and the right front wheel $FW_R$ of the vehicle are steered by means of a power steering unit 1. More specifically, the power steering unit 1 is equipped with a front steering actuator 3 having a hydraulic cylinder, and both piston rods of the front steering actuator 3 are connected to the left front wheel $FW_L$ and the right front wheel $FW_R$ via a tie rod 2.

The front steering actuator 3 incorporates a rack and pinion mechanism (not shown) which is connected to a steering wheel 4, and its rack is formed as one piston rod of the front steering actuator 3. Therefore, when the steering wheel 4 is operated, the front steering actuator 3 is driven via the rack and pinion mechanism.

The front steering actuator 3 is in fluid communication with a front steering valve 5. The front steering valve 5 is mechanically connected the steering wheel 4. Therefore, the front steering valve 5 can be operated by the steering wheel 4.

The front steering valve 5 is connected to one hydraulic pump 7 in a pump unit 6. That is, the plump unit 6 has a pair of hydraulic pumps 7, 9 which are tandem connected with each other. These hydraulic pumps are driven by a vehicle engine 8.

The other hydraulic pump 9 is connected to a rear steering actuator 11 via a rear steering valve 10. This rear steering actuator 11 includes a hydraulic cylinder similar to that in the above-mentioned front steering actuator 3. Both piston rods of the rear steering actuator 11 are connected to the left rear wheel $RW_L$ and the right rear wheel $RW_R$ via a tie rod 12. The suction ports of hydraulic pumps 7, 9 are connected to a reservoir tank 14.

When the steering wheel 4 is operated, the hydraulic fluid is fed from the hydraulic pump 7 to the front steering actuator 3 by the changeover of the front steering valve 5. As a result, the front steering actuator 3 operates in accordance with the rotational direction of steering wheel 4; thus, the front wheels FW are steered.

When the front wheels FW are steered, the rear wheels RW can also be steered via the rear steering valve 10 and the rear steering actuator 11. Since the rear steering valve 10 is electrically connected to a controller 15 as shown in FIG. 1, the controller 15 supplies a control signal $S_R$ to the rear steering valve 10 in accordance with the running condition of vehicle to control the changeover of the rear steering valve 10. As a result, the pressure and feeding direction of hydraulic fluid, which is fed from the hydraulic pump 9 to the rear steering actuator 11 via the rear steering valve 10, is controlled, and then the rear wheels $RW_L$ and $RW_R$ are steered.

The controller 15 is also electrically connected to the front steering valve 5, so that the front steering valve 5 can receive a control signal $S_F$ from the controller 15.

When the control signal $S_F$ is sent from the controller 15 to the front steering valve 5, the front steering valve 5 controls the feed pressure of hydraulic fluid to the front steering actuator 3 so as to advance the steering phase of front wheels FW in relation to the operation of steering wheel 4.

For the controller 15 to produce control signals $S_F$, $S_R$ which are to be fed to the steering valves 5, 10, the controller 15 is electrically connected to various sensors and meters. The meters supply detection signals indicating the operating conditions of various devices to the controller 15.

The above-mentioned sensors include a vehicle speed sensor 26 for detecting the vehicle speed, a sensor 16 for detecting the operating angle $\theta_H$ of steering wheel 4, a sensor 17 for detecting the actual steering angle $\delta_{Ra}$ of rear wheels RW, and a sensor for detecting the operating pressure of front steering actuator 3. Sensor signals from these sensors are fed to the controller 15.

In this embodiment, the sensor for detecting the operating pressure of front steering actuator 3 includes a pair of pressure sensors 18, 19. These pressure sensors 18, 19 detect the pressures in a right and left pressure chambers (not shown) in the front steering actuator 3, respectively, to send their sensor signals to the controller 15. The controller 15 calculates the pressure difference between the two pressure chambers on the basis of the sensor signals from a pair of pressure sensors 18, 19. This pressure difference is used as the operating pressure $\Delta P$ of front steering actuator 3.

Figure 2:
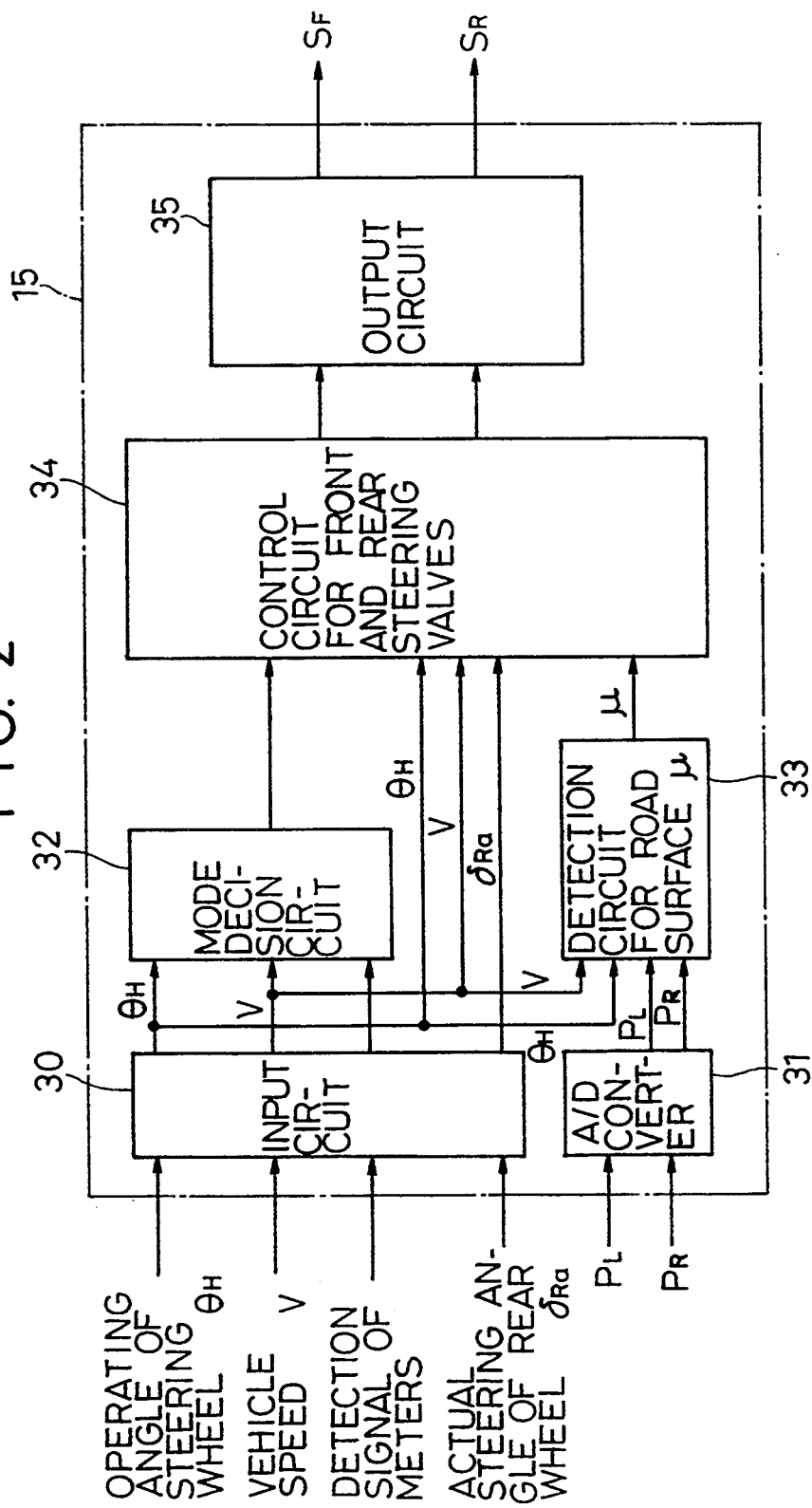
FIG. 2 is a block diagram showing a configuration of the controller in FIG. 1.

A typical internal circuit of controller 15 is shown in FIG. 2. The controller 15 has an input circuit 30 which receives the sensor signals indicating the operating angle $\theta_H$, of steering wheel 4, the vehicle speed V, and the actual steering angle $\delta_{Ra}$ of rear wheels RW from the sensors 16, 26, 17, respectively, and an analog/digital (A/D) converter 31 which receives the sensor signals indicating the pressures $P_L$, $P_R$ in the pressure chambers of front steering actuator 3 detected by the pressure sensors 18, 19, respectively. The input circuit 30 is connected to a decision circuit 32, which selects one steering control mode of the vehicle from a number of modes on the basis of the data supplied through the input circuit 30, namely, the data indicating the operating angle $\theta_H$, the vehicle speed V, and the actual steering angle $\delta_{Ra}$ of rear wheels RW, and the detection data from the meters. These steering control modes include an interruption mode of the steering control an opposite phase steering mode of the rear wheels RW in which the rear wheels RW are steered in the opposite phase with the front wheels FW when the vehicle speed is low and the operating angle $\theta_H$ is large (for example, $V \leq 30$ km/h and $\theta_H \geq 230°$); and a phase control mode in which the steering phases of front and rear wheels are controlled when the vehicle speed is in the medium and high speed range (for example, $V \geq 40$ km/h).

The input circuit 30 and the A/D converter 31 are connected to a detection circuit 33 for detecting the friction coefficient of road surface, namely the road surface $\mu$. The detection circuit 33, to which the data indicating the operating angle $\theta_H$ and the vehicle speed V are supplied from the input circuit 30 and the data indicating the pressures $P_L$, $P_R$ are supplied from the A/D converter 31, determines the road surface $\mu$ by calculating it on the basis of these data.

The decision circuit 32 and the detection circuit 33 are connected to a control circuit 34 for the front and rear steering valves 5, 10. This control circuit 34 receives the steering control mode selected by the decision circuit 32 and the data indicating the road surface $\mu$ determined by the detection circuit 33. As seen from FIG. 2, the control circuit 34 also receives the data indicating the operating angle $\theta_H$, the vehicle speed V and the actual steering angle $\delta_{Ra}$ supplied from the input circuit 30. On the basis of these supplied data, the control circuit 34 produces the above-mentioned control signals $S_F$, $S_R$. These signals $S_F$, $S_R$ are fed from the control circuit 34 to the front and rear steering valves 5, 10, respectively, via an output circuit 35.

Figure 3:
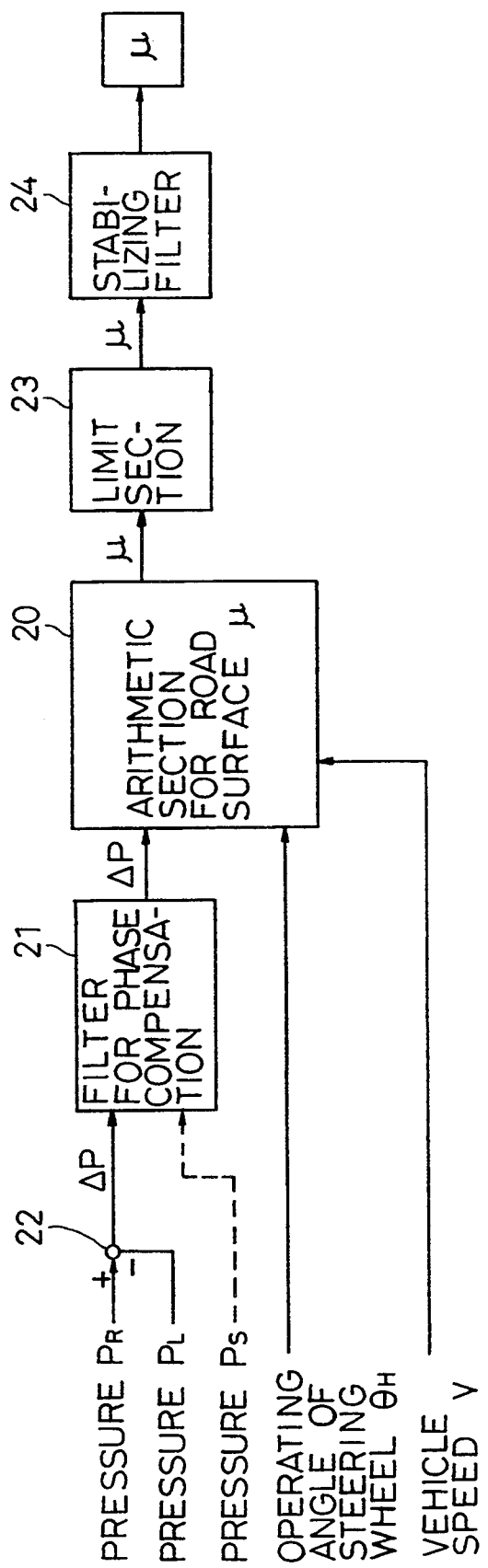
FIG. 3 is a block diagram showing a detection circuit for detecting road surface $\mu$ in FIG. 2.
Figure 4A:
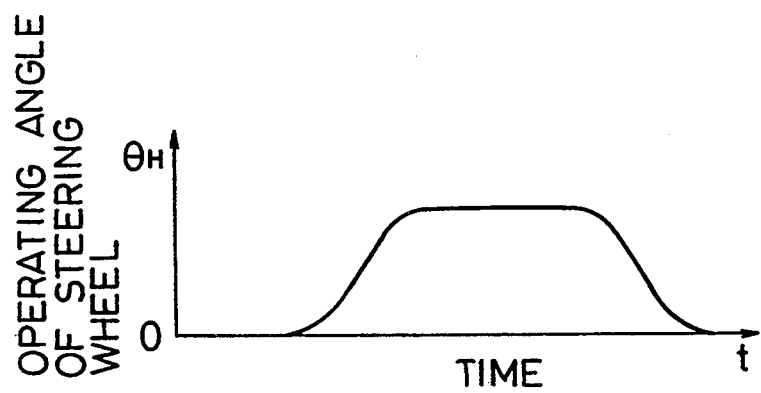
FIGS. 4A–4B are graphs showing relationships between the steering angle of front wheels and the operating pressure of power steering unit for front wheels.
Figure 4B:
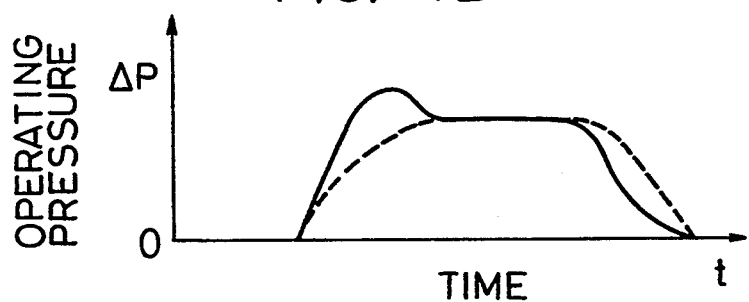

The specific procedure for calculating the road surface $\mu$ in the detection circuit 33 is shown in the block diagram of FIG. 3. As seen from FIG. 3, an arithmetic section 20 for road surface $\mu$ receives the operating pressure $\Delta P$ of front steering actuator 3, obtained from the pressures $P_L$, $P_R$ detected by the pressure sensors 18, 19, the operating angle $\theta_H$ detected by the sensor 16, and the vehicle speed V detected by the sensor 26. The operating pressure $\Delta P$ is calculated in a subtraction section 22 to which pressures $P_L$, $P_R$ are supplied, and then sent to the arithmetic section 20 through a filter 21 for phase compensation. The filter 21 serves two functions; it not only removes noise of operating pressure $\Delta P$ but also compensates the advance of phase of operating pressure $\Delta P$ in relation to the operating angle $\theta_H$ at the transition stage for the operation of steering wheel 4. At the start of the operation of steering wheel 4, the operating pressure $\Delta P$ of front steering actuator 3 increases suddenly as shown by the solid line in FIG. 4, and at the start of turning back of steering wheel 4, the operating pressure $\Delta P$ decreases suddenly. This means that a phase difference occurs in the change tendency of the operating angle $\theta_H$ and the operating pressure $\Delta P$. However, the phase difference between the operating angle $\theta_H$ and the operating pressure $\Delta P$ is compensated in the filter 21, so that the operating pressure $\Delta P$ increases and decreases with the change in the operating angle $\theta_H$ as shown by the broken line in FIG. 4.

The phase difference between the operating angle $\theta_H$ and the operating pressure $\Delta P$ is produced by the operating characteristics of front steering valve 5 itself and the tire inertia effect.

In the arithmetic section 20, the road surface $\mu$ is calculated on the basis of the operating pressure $\Delta P$, the operating angle $\theta_H$ and the vehicle speed V. The principle of calculating the road surface $\mu$ will be explained below by referring to FIG. 5.

Figure 5:
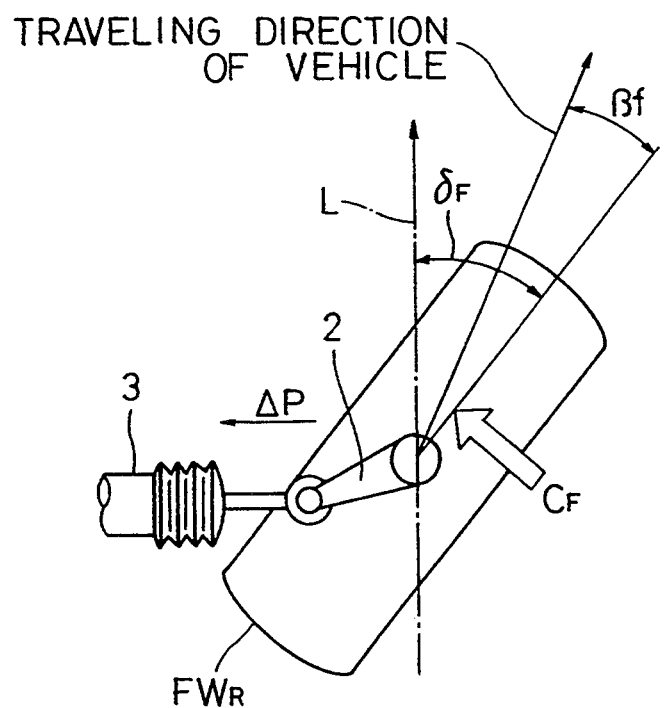
FIG. 5 is a schematic view showing a cornering force occurring on the front wheels in relation to the slip angle of front wheels.

When the front wheels FW are steered, the cornering force $C_F$ of the right front wheel $FW_R$ is expressed by the following equation:

$$C_F \propto \beta f \cdot \mu$$

where, $\beta f$ is an inclination angle or a slip angle of right front wheel $FW_R$ in relation to the traveling direction of right front wheel $FW_R$ as shown in FIG. 5.

Figure 6:
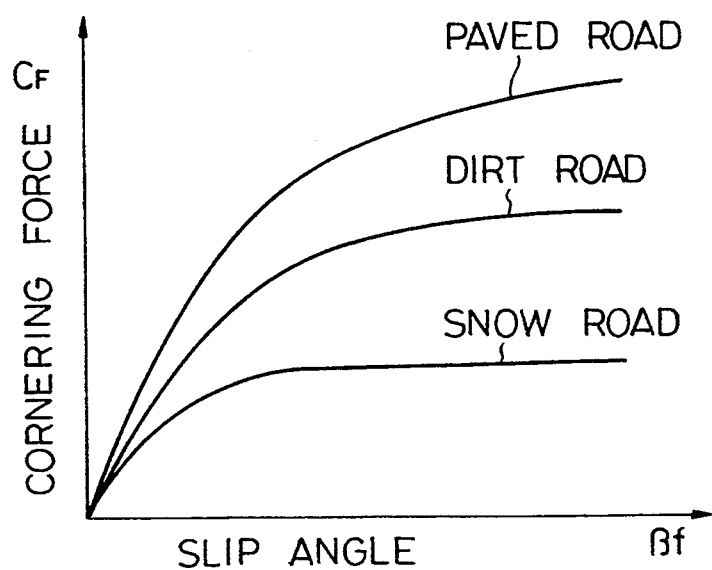
FIG. 6 is a graph showing relationships between the cornering force and the slip angle of front wheels for road surfaces having a different friction coefficient.

As seen from the above equation, the cornering force $C_F$ is proportional to the product of slip angle $\beta f$ and road surface $\mu$. Therefore, if the road surface $\mu$ is different, that is, the condition of road surface is different, the cornering force $C_F$ of front wheel differs greatly even if the slip angle $\beta f$ is equal. Specifically, the cornering force $C_F$ of front wheel increases as the road surface $\mu$ increases, in the range where the slip angle $\beta f$ is large as shown in FIG. 6. In FIG. 5, reference symbol L denotes the line in parallel with the vehicle body axis, and reference symbol $\delta_F$ denotes the steering angle of right front wheel $FW_R$, namely the front wheels FW.

As seen from FIG. 5, considering the dynamic equilibrium condition, the cornering force $C_F$ and the operating pressure $\Delta P$ of front steering actuator 3 are in a nearly proportional relationship. Therefore, using the operating pressure $\Delta P$ in place of the cornering force $C_F$, the above equation can be rewritten as follows:

$$\Delta P = C_1 \cdot \beta f \cdot \mu \tag{1}$$

where, $C_1$ is a constant.

The slip angle $\beta f$ is expressed by the following equation as a function of vehicle speed V, operating angle $\theta_H$, and road surface $\mu$.

$$\beta f = C_3 \cdot V^2 \cdot \theta_H / (\mu + C_2 \cdot V^2) \tag{2}$$

where, $C_2$ and $C_3$ are constants.

From Equations (1) and (2), the ratio of the operating pressure $\Delta P$ to the operating angle $\theta_H$, $\Delta P/\theta_H$, is expressed by the following equation:

$$\Delta P/\theta_H = \mu \cdot C_1 \cdot C_3 \cdot V^2 / (\mu + C_2 \cdot V^2) \tag{3}$$

In the arithmetic section 20, therefore, the road surface $\mu$ is calculated from Equation (3) by putting the values of vehicle speed V, operating angle $\theta_H$ and operating pressure $\Delta P$ into Equation (3).

The calculated road surface $\mu$ is output through a limit section 23 and a stabilizing filter 24. The limit section 23 supplies the road surface $\mu$ as it is to the stabilizing filter 24 if the change rate of road surface $\mu$ supplied from the arithmetic section 20 is within the allowable range. Further, it stops the output of road surface $\mu$ to the stabilizing filter if the change rate of road surface $\mu$ is outside the above allowable range. The limit section 23 may output the road surface $\mu$ obtained by limiting its change rate to the maximum or minimum value to the stabilizing filter 24 if the change rate of road surface $\mu$ is outside the above allowable range. The stabilizing filter 24 serves a function of stabilizing and outputting the value of road surface $\mu$ supplied from the limit section 23.

Figure 7:
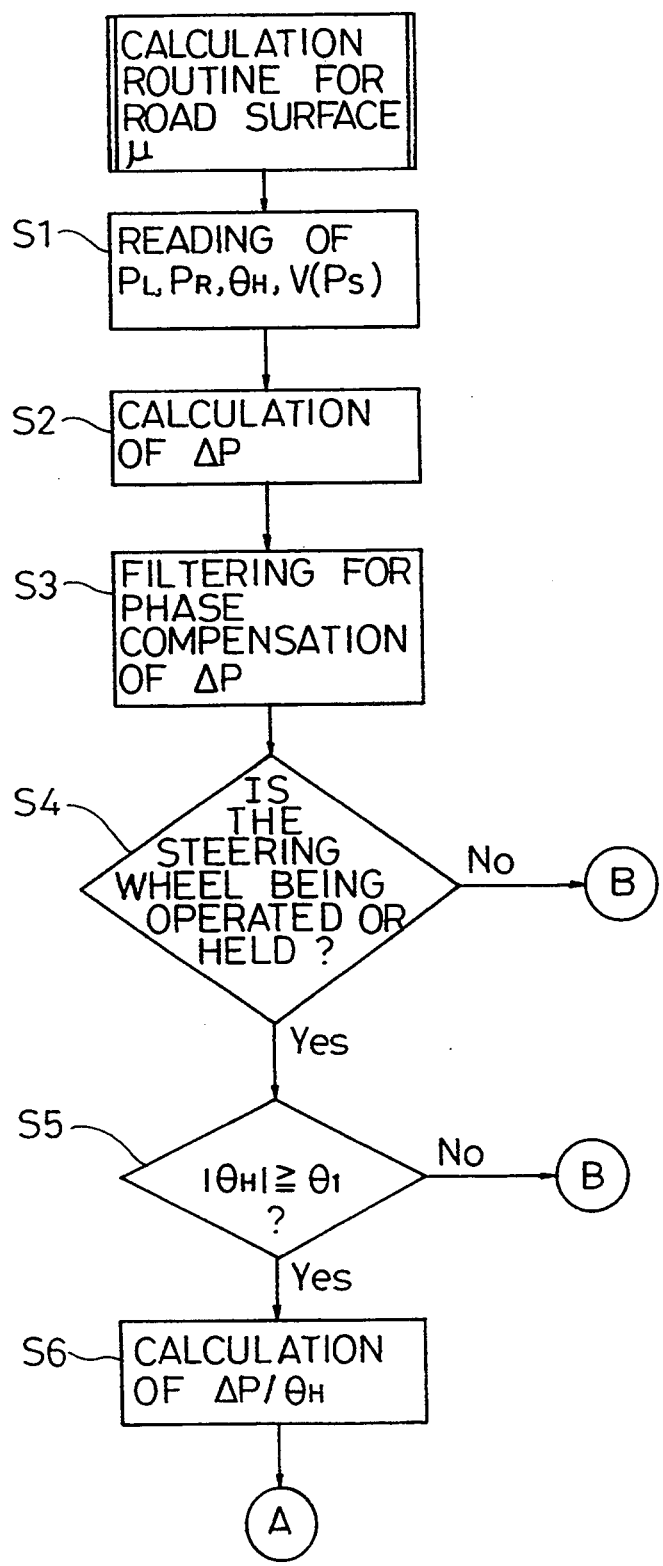
FIGS. 7 and 8 are flowcharts showing a routine for calculating road surface $\mu$.
Figure 8:
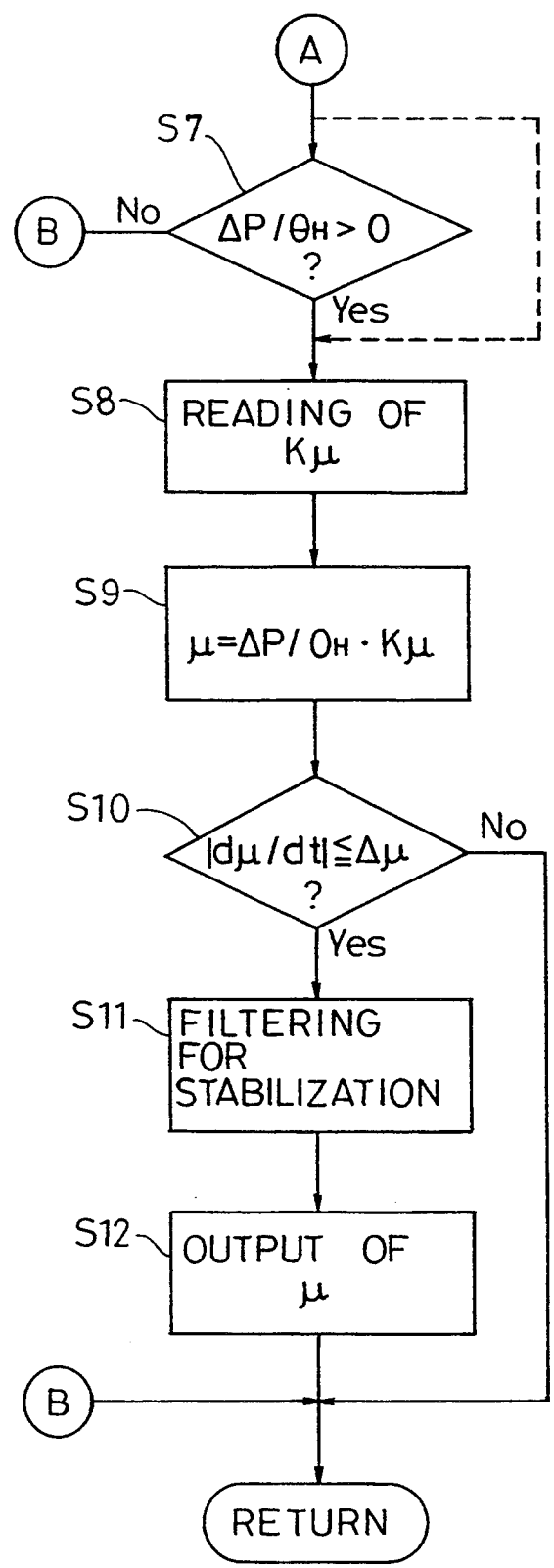

The above-described calculating procedure for the road surface $\mu$ shown by the block diagram in FIG. 3 becomes apparent upon making reference to the calculation routine for road surface $\mu$ shown by a flowchart in FIGS. 7 and 8. Therefore, the calculation routine will be explained below.

Calculation Routine for Road Surface $\mu$

First, in Step S1 in FIG. 7, the operating angle $\theta_H$, pressures $P_L$, $P_R$ and vehicle speed V detected by the sensors 16, 18, 19 and 26, are read.

Next, in Step S2, the pressure difference between the pressures $P_L$ and $P_R$, namely the operating pressure $\Delta P$ ($=P_R-P_L$) of front steering actuator 3 is calculated. Then, the operating pressure $\Delta P$ is filtered in the above-mentioned filter 21 for phase compensation in Step S3.

In Step S4, a decision is made on whether the steering wheel 4 is being operated or held at a rotational angle position or not. This decision is made on the basis of the magnitude and change direction of operating angle $\theta_H$ of steering wheel 4.

When the decision result in Step S4 is NO, namely when the steering wheel 4 is turned back, the flow returns to Step S1 and the above steps are repeated as shown in the flowchart of FIG. 8.

When the decision result in Step S4 is YES, namely when the steering wheel 4 is turned or held at a rotational angle position, the flow proceeds to Step S5.

In Step S5, a decision is made on whether the absolute value of the operating angle $\theta_H$ of steering wheel 4 is not lower than a predetermined positive value $\theta_1$ (for example, 10°) or not. When the decision result in this step is NO, namely the absolute value of the operating angle $\theta_H$ is smaller than the positive value $\theta_1$, it is decided that the steering wheel 4 has not yet been turned. Thus, the flow returns from Step S5 to Step S1 so that the steps are repeated from the beginning.

When the decision result in Step S5 is YES, namely the absolute value of the operating angle $\theta_H$ is not lower than the positive value $\theta_1$, the flow proceeds to Step S6, where the ratio of the operating pressure $\Delta P$ to the operating angle $\theta_H$, $\Delta P/\theta_H$, is calculated.

Then, the flow goes from Step S6 to Step S7 in FIG. 8, in which another decision is made. In this step, a decision is made on whether the direction in which the front wheels FW are steered by the front steering actuator 3 on the basis of the operating pressure $\Delta P$ is in agreement with the direction in which the front wheels FW are steered on the basis of the operating angle $\theta_H$ of steering wheel 4, in other words, whether the sign of $\Delta P/\theta_H$ is positive or not. When the decision result is NO, it is determined that the vehicle is slaloming and the steering wheel 4 is being operated by repeating turning and back turning, or that the phase of change of operating pressure $\Delta P$ is opposite to that of the operating angle $\theta_H$ in spite of the filtering in Step S3. In this case, the flow returns from Step S7 to Step S1 so that the steps are repeated from the beginning.

Figure 9:
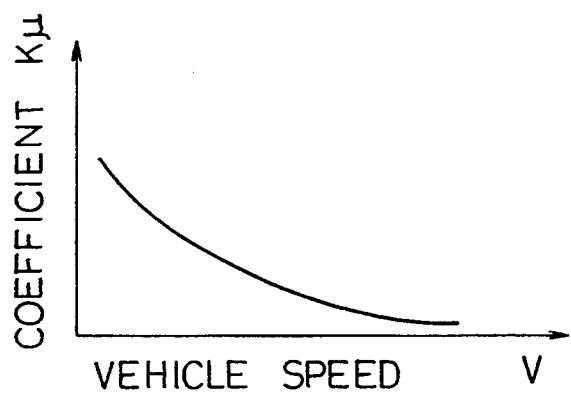
FIG. 9 is a graph showing coefficient K$\mu$ as a function of the vehicle speed.

When the decision result in Step S7 is YES, the flow goes to Step S8, in which a coefficient $K\mu$ used for calculating the road surface $\mu$ is determined. Specifically, the coefficient $K\mu$ is read from a map that represents the coefficient $K\mu$ as a function of the vehicle speed V as shown in FIG. 9. This map has been stored in advance in memory (not shown) in the detection circuit 33 in FIG. 2.

The coefficient $K\mu$ is equivalent to the equation in brackets [ ] in the following equation, which is obtained by rewriting Equation (3).

$$\mu = [1 + C_2 \cdot V^2/(C_1 \cdot C_3 \cdot V^2)] \cdot \Delta P/\theta_H \quad (4)$$

Therefore, the coefficient $K\mu$ can be expressed by the following equation:

$$K\mu = 1 + C_2 \cdot V^2/(C_1 \cdot C_3 \cdot V^2) \quad (5)$$

Therefore, the map in FIG. 9 can be represented as a function of the vehicle speed V as seen from Equation (5).

In Step S9, the value of coefficient $K\mu$ read in Step S8 is multiplied by the value of $\Delta P/\theta_H$ determined in Step S7 in FIG. 7 to calculate the road surface $\mu$. That is, the road surface $\mu$ can be calculated by inserting the value of $\Delta P/\theta_H$ and the value of vehicle speed V into Equation (4).

In Step S10, a decision is made on whether the absolute value of change rate for the calculated road surface $\mu$, namely the absolute value of the differentiation result of road surface $\mu$ ($=d\mu/dt$), is within a predetermined value $\Delta\mu$ (for example, 0.2 $\mu$/sec) or not. When the decision result is NO, the flow returns to Step S1. On the other hand, when the result is YES, filtering is carried out to stabilize the value of the calculated road surface $\mu$ in Step S11, and then the road surface $\mu$ is finally output in Step S12.

According to the above-described embodiment, the road surface $\mu$ is detected each time the steering wheel 4 is operated on running the vehicle. Therefore, the steering angle $\delta_R$ of rear wheels RW can be controlled on the basis of the latest value of road surface $\mu$. Even if the road surface condition changes, the road surface $\mu$ is detected at the time when the steering wheel 4 is operated, so that the optimum steering control of rear wheels RW is performed in accordance with the road surface condition, namely the road surface $\mu$, resulting in some improvement in steering stability of the vehicle.

Since the operating pressure $\Delta P$ of front steering actuator 3 is calculated on the basis of the sensor signals sent from the pressure sensors 18 and 19, and then filtered for phase compensation, the advance of phase of the operating pressure $\Delta P$ in relation to the steering angle $\theta_H$ can be prevented at the operating transition stage of the steering wheel 4.

In calculating the road surface $\mu$, an exact value of road surface $\mu$ can be obtained since the road surface $\mu$ is calculated in Step S9 only when all the decision results in Steps S4, S5 and S7 are YES. The YES decision results in Steps S4 and S5 mean that the steering wheel 4 is operated so that the absolute value of operating angle $\theta_H$ of the steering wheel 4 is not smaller than the specified value $\theta_1$ or the steering wheel 4 is held at a predetermined rotational angle position. In this case, since the front wheels FW are steered by the front steering actuator 3, the operating pressure $\Delta P$ of the front steering actuator 3 is in the condition of actual increase. As a result, the road surface $\mu$ can be exactly calculated on the basis of the operating pressure $\Delta P$. The YES decision result in Step S7 means that the steering direction of front wheels FW on the basis of the operating pressure $\Delta P$ is in agreement with the steering direction of front wheels FW on the basis of the operating angle $\theta_H$. Therefore, the road surface $\mu$ can be calculated by precluding the adverse effects of the characteristics of front steering valve 5 and the inertia of front wheel FW tires. This also improves the accuracy of the calculated value of road surface $\mu$.

When either of decision results in Steps S4, S5 or S7 is NO, a new road surface $\mu$ is not calculated since Step S8 and the subsequent steps are not performed. In this case, the previously calculated value is kept.

Further, according to the above-described embodiment, even when the road surface $\mu$ is calculated in Step S9, this calculated road surface $\mu$ is not immediately output, but is output through the executions in Steps S10 and S11. The execution in Step S10 means that the value of calculated road surface $\mu$ is changed into a new value only when the absolute value of road surface $\mu$ is within the specified value $\Delta\mu$. Furthermore, since the road surface $\mu$ is finally output through the filtering operation for stabilization, a sudden change in the value of road surface $\mu$ does not occur, and a stabilized output value of road surface $\mu$ is produced.

The road surface $\mu$ calculated by the above-described routine is supplied from the detection circuit 31 to the control circuit 34 for controlling the steering valves. In this control circuit 34, the steering angle $\delta_R$ of rear wheels RW is calculated from the road surface $\mu$, the operating angle $\theta_H$ and the vehicle speed V as described above. The procedure for calculating the steering angle $\delta_R$ in the control circuit 34 is shown by the block diagram in FIG. 10.

Figure 10:
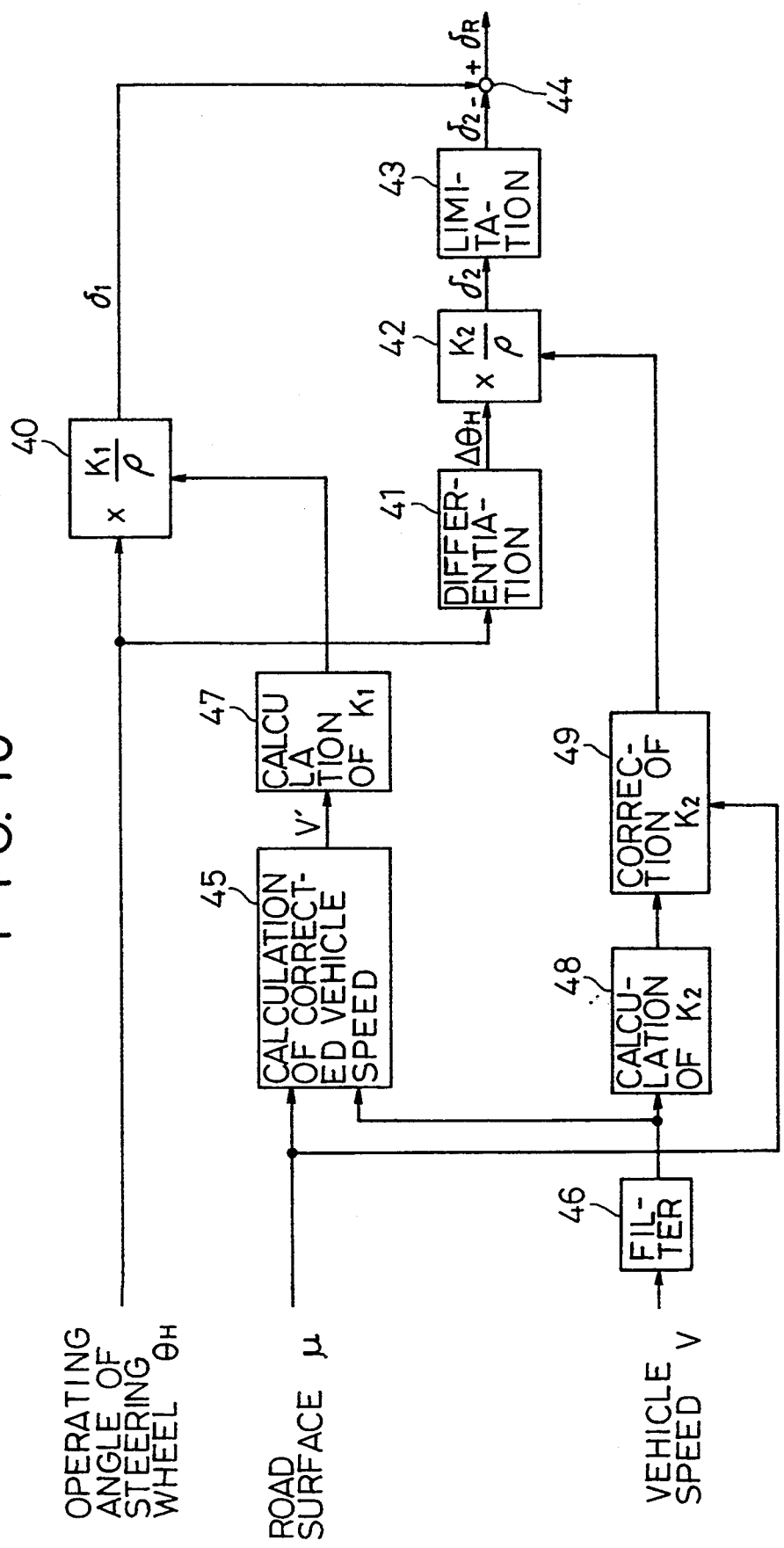
FIG. 10 is a block diagram showing the function of control circuit for a rear steering valve of FIG. 1.

For explanation by referring to the block diagram in FIG. 10, it is assumed that the phase control mode has been selected in the decision circuit 32 in FIG. 2. This block diagram, being for calculating the steering angle $\delta_R$ of rear wheels RW, does not indicate the control for advancing the steering phase of front wheels FW in relation to the operating angle $\theta_H$ of steering wheel 4.

First, the operating angle $\theta_H$ of steering wheel 4 is supplied to an amplification section 40, where a steering angle $\delta_1$ of the rear wheels RW is calculated by multiplying the operating angle $\theta_H$ by $(K_1/\rho)$. This steering angle $\delta_1$ represents the steering amount for steering the rear wheels RW to the same direction as the steering direction of front wheels FW, namely in the same phase. $K_1$ is the so-called equiphase coefficient, and $\rho$ is the steering gear ratio.

The operating angle $\theta$hd H is also supplied to a differentiation section 41, where the angular velocity $\Delta\theta_H$ of steering wheel 4 is calculated. Then, the calculated angular velocity $\Delta\theta_H$ is multiplied by $(K_2/\rho)$, so that a steering angle $\delta_2$ of rear wheels RW is calculated, in another amplification section 42. The steering angle $\delta_2$ represents the steering amount for steering the rear wheels RW in the direction opposite to the steering direction of front wheels FW, namely in the opposite phase. Therefore, $K_2$ represents the opposite phase coefficient.

The steering angle $\delta_2$ of opposite phase is then supplied to a limit section 43. This limit section 43 outputs the steering angle $\delta_2$ when the absolute value of steering angle $\delta_2$ is not smaller than a predetermined value (for example, 0.03°), but it sets the steering angle $\delta_2$ at 0° and outputs it when the absolute value of steering angle $\delta_2$ is smaller than the predetermined value.

The steering angles $\delta_1$, $\delta_2$ of rear wheels RW calculated in the multiplication section 40 and the limit section 43 are supplied to a subtraction section 44, where the steering angle $\delta_R$ of rear wheels RW is calculated by subtracting the steering angle $\delta_2$ from the steering angle $\delta_1$.

Summarization of the above-described calculation procedure for the steering angle $\delta_R$ of rear wheels RW, namely the calculation procedure carried out in sections 40 through 42, gives the following equation:

$$\delta_R = \delta_1 - \delta_2 = \theta_H \cdot (K_1/\rho) - \Delta\theta_H \cdot (K_2/\rho) \tag{6}$$

Then, in the control circuit 34 of FIG. 2, the difference between the steering angle $\delta_R$ calculated as described above and the actual steering angle $\delta_{Ra}$ of rear wheels RW is calculated. The control signal $S_R$ based on this difference is sent from the control circuit 34 to the rear steering valve 10 via the output circuit 35. When the rear steering valve 10 receives the control signal $S_R$, the rear steering valve 10 controls the operating pressure supplied to the rear steering actuator 11 and the supply direction of the operating pressure. Thus, the rear steering actuator 11 operates to match the actual steering angle $\delta_{Ra}$ of rear wheels RW to the steering angle $\delta_R$.

The above-mentioned equiphase coefficient $K_1$ and opposite phase coefficient $K_2$ are usually determined on the basis of the vehicle speed V. In this embodiment, however, the equiphase coefficient $K_1$ and opposite phase coefficient $K_2$ are determined by considering the detected road surface $\mu$ in addition to the vehicle speed V.

As seen from FIG. 10, the detected road surface $\mu$ is supplied to an arithmetic section 45, to which the vehicle speed V is also supplied after being filtered in a filter section 46. In the arithmetic section 45, the corrected vehicle speed V' is calculated by the following equation:

$$V' = V + (1-\mu) \cdot K_v \tag{7}$$

where, $K_v$ is a standard value for correcting the vehicle speed V, which is set at 20 km/h, for example.

The corrected vehicle speed V' calculated by Equation (7) is supplied to another arithmetic section 47, where the equiphase coefficient $K_1$ is calculated from the corrected vehicle speed V'. Specifically, in this embodiment the equiphase coefficient $K_1$ can be determined as a function of the corrected vehicle speed V' as indicated by the solid line in FIG. 11.

Figure 11:
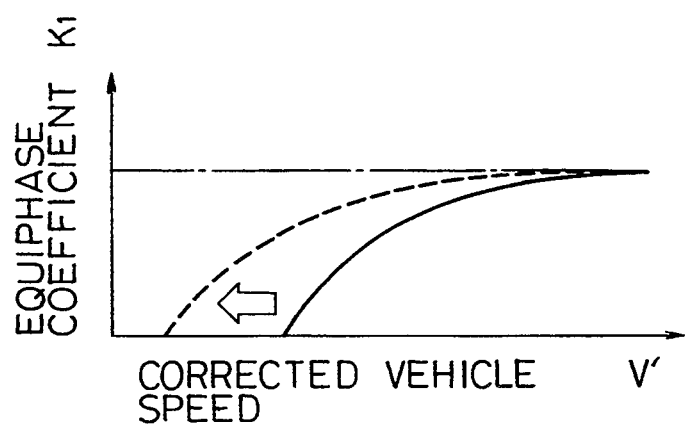
FIG. 11 is a graph showing an equiphase coefficient for the steering angle of rear wheels as a function of the vehicle speed.

As shown by the solid line in FIG. 11, the equiphase coefficient $K_1$ begins increasing as the corrected vehicle speed V' increases from the medium speed range (for example, about 60 km/h), and levels off when the corrected vehicle speed V' reaches the high speed range.

The solid line in FIG. 11 indicates the feature of the equiphase coefficient $K_1$ for high road surface $\mu$, namely in the case where the road surface has a high $\mu$ value. The solid line map in FIG. 11 is stored in advance in memory (not shown) in the control circuit 34 in FIG. 2.

As seen from the above equation for calculating the corrected vehicle speed V' and the map in FIG. 11, the value of the second term of the equation (7), $(1-\mu) \cdot Kv$, increases as the value of road surface $\mu$ decreases. Therefore, the corrected vehicle speed V' is further higher than the actual vehicle speed V as the road surface $\mu$ decreases. This means that in FIG. 11, the characteristic curve indicated by the solid line shifts to the left in the direction of the horizontal axis of the figure as shown by the broken line as the road surface $\mu$ decreases. As a result, when the road surface $\mu$ is low and the vehicle speed is in the medium speed range, the equiphase coefficient $K_1$ is increased in accordance with the decrease in road surface $\mu$. The equiphase coefficient $K_1$ determined this way in the arithmetic section 47 is supplied to the above-mentioned amplification section 40 and used in calculating the steering angle $\delta_1$.

Figure 12:
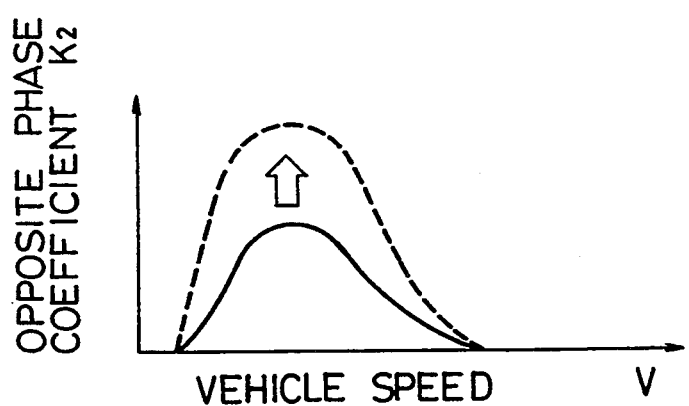
FIG. 12 is a graph showing the opposite phase coefficient for the steering angle of rear wheels as a function of the vehicle speed.

The vehicle speed V is also supplied to an arithmetic section 48 after being filtered in the filter section 46. In the arithmetic section 48, the opposite phase coefficient $K_2$ is calculated. Specifically, the opposite phase coefficient $K_2$ is determined from the vehicle speed V in accordance with the map in FIG. 12. As seen from the solid line in FIG. 12, the opposite phase coefficient $K_2$ reaches its maximum value when the vehicle speed V is in a relatively low speed range, for example, the vehicle speed V is about 30 km/h, and decreases when the vehicle speed V decreases or increases from the speed of about 30 km/h. The solid line in FIG. 12, like that in FIG. 11, indicates the feature for high road surface $\mu$. The map in FIG. 12 is also stored in memory in the control circuit 34 in FIG. 2.

The opposite phase coefficient $K_2$ determined in the arithmetic section 48 is then supplied to an arithmetic section 49, where the opposite phase coefficient $K_2$ is corrected. Specifically, the opposite phase coefficient $K_2$ is corrected on the basis of the road surface $\mu$ by using the following equation:

$$K_2 = K_2 \cdot (a - b \cdot \mu) \quad (8)$$

where, a and b are constants.

As shown by Equation (8), when the road surface $\mu$ decreases, the opposite phase coefficient $K_2$ is increased in accordance with the decrease in road surface $\mu$. This means that the feature shown by the solid line changes into the feature shown by the broken line in FIG. 12.

The opposite phase coefficient $K_2$ corrected in the arithmetic section 49 is supplied to the above-mentioned amplification section 42 and used for calculating the opposite phase steering angle $\delta_2$.

As described above, if the vehicle speed V' is corrected in accordance with the value of road surface, the corrected vehicle speed V' calculated by Equation (7) increases when the road surface $\mu$ is low. Thus, the equiphase coefficient $K_1$ increases when the road surface $\mu$ is low and the vehicle speed V is in the medium speed range, namely when the vehicle is running at a speed in the medium speed range on a road with a low $\mu$ as shown by the broken line in FIG. 11. In this case, the equiphase steering angle $\delta_1$ of rear wheels RW increases, therefore, the amount of steering to the equiphase side, contained in the steering angle $\delta_R$ of rear wheels RW in relation to the steering of front wheels FW, increases as shown in Equation (6). Consequently, when the front wheels FW are steered on running at a speed in the medium speed range on a road with a low $\mu$, the amount of steering of the rear wheels RW in the equiphase with the front wheels FW increases, so that the spinning of vehicle is effectively prevented and the steering stability of vehicle is improved.

When the vehicle speed V is in the high speed range, the equiphase coefficient $K_1$ is not increased even when the road surface $\mu$ is low and the corrected vehicle speed V' increases in accordance with Equation (7), as seen from the above explanation. Therefore, the amount of steering of the rear wheels RW in the equiphase with the front wheels FW does not further increase when the front wheels FW is steered. This means that the amount of steering of the rear wheels RW in the equiphase does not increase when the front wheels FW is steered, even if the corrected vehicle speed V' is in the high speed range in the condition where it has been decided that the road has a low $\mu$ though it has really a high $\mu$ due to an error in detecting the road surface $\mu$. Consequently, undesirable and excessive steering of the rear wheels RW in the equiphase with the front wheels FW is prevented in the above-described condition, providing fail-safe steering.

Figure 13:
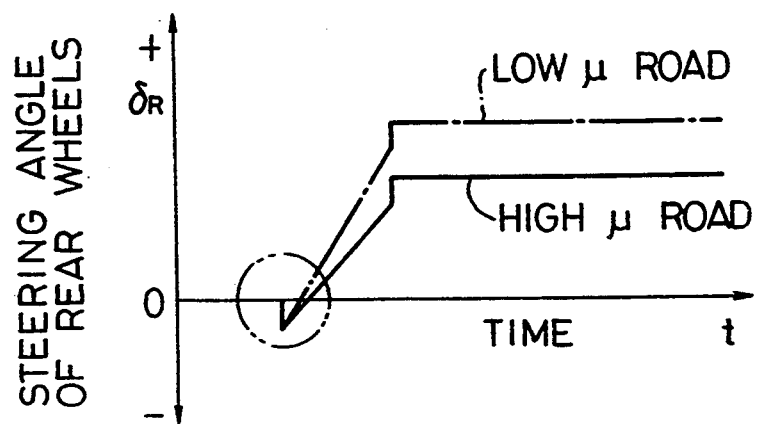
FIG. 13 is a graph showing a difference in steering angle of rear wheels between that which occurs on a high $\mu$ road and that which occurs on a low $\mu$ road.

The opposite phase coefficient $K_2$ is corrected so as to be increased as shown by the broken line in FIG. 12 and as seen from Equation (8) when the vehicle speed V is in a relatively low speed range and the road surface $\mu$ is low. In this case, the opposite phase steering angle $\delta_2$ in Equation (6), namely the amount of steering of the rear wheels RW in the direction opposite to the steering direction of front wheels FW increases when the change rate of operating angle $\theta_H$ at the steering wheel 4, namely the angular velocity $\Delta\theta_H$ is increased by the relatively rapid operation of steering wheel 4. This means that in the change characteristics of steering angle $\delta_R$ of the rear wheels RW shown in FIG. 13, the amount of instantaneous steering of rear wheels RW in the opposite phase in the area encircled by the alternate long and two short dashes line increases. Consequently, when the steering wheel 4 is operated while the vehicle is running at a relatively low speed on a road with a low $\mu$, the turning ability of the vehicle is improved, assuring high steering stability on roads with a low $\mu$.

The above-described steering control method for the rear wheels, needless to say, improves the delay in response to the lateral acceleration and yawing acting on the vehicle in relation to the operation of steering wheel 4.

The control for advancing the phase of steering angle $\delta_F$ of the front wheels FW in relation to the operating angle $\theta_H$ of steering wheel 4 will be briefly explained below. This control is to increase the steering angle $\delta_F$ of front wheels FW in accordance with the angular velocity $\Delta\theta_H$ of steering wheel 4. To do this, the steering angle $\delta_F$ of the front wheels FW is calculated by adding $\Delta\theta_H \cdot K_3/\rho$ to the value obtained from the operating angle $\delta_H$ of steering wheel 4, and the control signal $S_F$ on the basis of the calculated steering angle $\delta_F$ is fed to the front steering valve 5.

$K_3$ is a coefficient for advancing the phase. It varies with the vehicle speed V, like the opposite phase coefficient $K_2$ in FIG. 12, and also varies with the value of road surface $\mu$, like the opposite phase coefficient $K_2$. If the phase of steering angle $\delta_F$ of the front wheels FW is advanced in the above-described manner, the response to yawing acting on the vehicle body while the vehicle is turning can be further improved.

This invention is not limited to the above-described embodiment, but can be carried out in many variations. For example, though the operating pressure $\Delta P$ of front steering actuator 3 is calculated from the sensor signals from a pair of pressure sensors 18 and 19 in the above-described embodiment, the operating pressure $\Delta P$ can be determined by a single pressure sensor in place of the pressure sensors 18 and 19. In this case, a pressure sensor 25 is disposed near the discharge port of hydraulic pump 7 as shown in FIG. 1. The pressure sensor 25 detects the discharge pressure of hydraulic pump 7. The discharge pressure $P_s$ of hydraulic pump 7 is supplied to the filter 21 for phase compensation as shown in the block diagram in FIG. 3. In Step S1 in FIG. 7, the discharge pressure $P_s$ is read in place of the pressures $P_L$ and $P_R$, and Step S7 in the flowchart in FIG. 8 is bypassed as shown by the broken line.

In the flowchart in FIG. 7, Step S4 may decide on only whether the steering wheel 4 is operated or not. In this case, the road surface $\mu$ is not calculated when the steering wheel 4 is held at the specified rotational position or it is turned back.

Although the coefficients $K_1$, $K_2$ and $K_3$ are corrected so as to be increased as the road surface $\mu$ decreases, they may be corrected so that only the equiphase coefficient $K_1$ is increased with decreasing road surface $\mu$. In carrying out this invention, the above-described control for advancing the steering phase of front wheels FW is not necessarily needed.

It is to be understood that the present invention is not limited to the above-described embodiments, and that various changes and modifications may be made in the invention without departing from the spirit and the scope of the invention as hereinafter claimed.

What is claimed is:

1. A method for detecting a friction coefficient of a road surface on which a vehicle runs, the vehicle including front wheels, a steering wheel and a hydraulic power steering unit disposed between the front wheels and the steering wheel, the hydraulic power steering unit assisting the steering wheel in steering the front wheels, the method comprising the steps of:

(a) detecting an operating angle of the steering wheel, a speed of the vehicle and an operating pressure of the hydraulic power steering unit, respectively;

(b) detecting a proper steering situation only when at least one of two conditions is satisfied during operation of the steering wheel, one condition being an increase in steering angle of the front wheels and the other condition being the holding of the front wheels at a steering position beyond a predetermined angle and (c) calculating a friction coefficient of the road surface on the basis of the data detected in said step (a) only when the proper steering situation is detected in said step (b), the friction coefficient of the road surface being calculated by using relationships of the following three conditions, (i) a slip angle of the front wheels is determined in accordance with the detected operating angle of the steering wheel, the detected vehicle speed and the friction coefficient of the road surface, (ii) a cornering force of the front wheels is determined in accordance with the slip angle and the friction coefficient of the road surface, and (iii) the cornering force is proportional to the detected operating pressure of the hydraulic power steering unit.

2. The method according to claim 1, wherein said step (b), when the absolute value of the operating angle of the steering wheel is at least equal to a predetermined value in addition to said condition being satisfied, this is detected as the proper steering situation in step (b).

3. The method according to claim 1, wherein said step (a) includes a filtering process for compensating a phase advance of the operating pressure in relation to the operating angle of the steering wheel.

4. The method according to claim 1, wherein the hydraulic power steering unit has right and left pressure chambers, and a pressure difference between the right and left pressure chambers is detected as the operating pressure of the hydraulic power steering unit.

5. The method according to claim 4, wherein said step (b), when a steering direction of the front wheels, determined on the basis of a direction in which the operating pressure, is in agreement with a steering direction of the front wheels, determined on the basis of the operating angle of the steering wheel, in addition to said condition being satisfied, this is detected as the proper steering situation in said step (b).

6. The method according to claim 1, wherein in said step (c), when the operating angle of the steering wheel detected in said step (a) is denoted by $\theta_H$, the vehicle speed by V and the operating pressure of the hydraulic power steering unit by $\Delta P$, the friction coefficient $\mu$ of the road surface is expressed as $$\mu = K\mu \cdot \Delta P / \theta_H$$

where, $K\mu$ is a coefficient expressed as $$K\mu = 1 + C_2 \cdot V^2 / (C_1 \cdot C_3 \cdot V^2)$$

where, $C_1$, $C_2$ and $C_3$ are constants.

7. The method according to claim 1, wherein the method further includes a step (d) executed after said step (c), and said steps (a)–(d) are executed repeatedly, said step (d) including calculating a change rate of the friction coefficient of the road surface on the basis of the friction coefficient determined in said step (c), and outputting the friction coefficient of the road surface calculated in the most recently executed step (c) as it is when the absolute value of the calculated change rate of the friction coefficient in at most equal to a predetermined value, and maintaining and outputting the friction coefficient of the road surface calculated in the previous step (c) when the absolute value of the calculated change rate of the friction coefficient is larger than the predetermined value.

8. The method according to claim 1, wherein the method further includes step (e), filtering to stabilize the calculated friction coefficient of the road surface.

9. The method according to claim 1, wherein the hydraulic power steering unit includes a steering actuator disposed between the front wheels and the steering wheel, a hydraulic pump for supplying hydraulic fluid to the steering actuator and a front steering valve disposed between the hydraulic pump and the steering actuator for controlling a flow direction of the hydraulic fluid from the hydraulic pump to the steering actuator, and in said step (a), the operating pressure of the hydraulic power steering unit is detected on the basis of the fluid pressure between the front steering valve and the hydraulic pump.

10. An apparatus for detecting a friction coefficient of a road surface on which a vehicle is running, the vehicle including front and rear wheels, a steering wheel and a hydraulic power steering unit disposed between the front wheels and the steering wheel, the hydraulic power steering unit assisting the steering wheel in steering the front wheels, and the apparatus comprising;

first means for detecting an operating angle of the steering wheel;

second means for detecting a vehicle speed;

third means for detecting an operating pressure of the hydraulic power steering unit in proportion to a cornering force of the front wheels; and calculating means for calculating a friction coefficient of the road surface on the basis of the operating angle of the steering wheel, the vehicle speed and the operating pressure detected by said first, second and third means, said calculating means including detection means for detecting a proper steering situation only when at least one of two conditions is satisfied during operation of wheel, one condition being an increase in steering angle of the front wheels and the other condition being the holding of the front wheels at a steering position beyond a predetermined angle, and fourth means for calculating a friction coefficient of the road surface by using relationships of the following three conditions, (i) a slip angle of the front wheels is determined in accordance with the detected operating angle of the steering wheel, the detected vehicle speed and the friction coefficient of the road surface, (ii) a cornering force of the front wheels is determined in accordance with the slip angle and the friction coefficient of the road surface, and (iii) the cornering force is proportional to the detected operating pressure of the hydraulic power steering unit.

11. A four-wheel steering method of a vehicle, the vehicle including a steering wheel, front wheels steered by the steering wheel, and hydraulic power steering unit disposed between the front wheels and the steering wheel, the hydraulic power steering unit assisting the steering wheel in steering the front wheels, and rear wheels which can be steered in accordance with the steering of the front wheels, the method comprising the steps of:
(a) detecting an operating angle of the steering wheel, a speed of the vehicle and an operating pressure of the hydraulic power steering unit, respectively;
(b) detecting a proper steering situation only when at least one of two conditions is satisfied during operation of the steering wheel, one condition being an increase in the steering angle of the front wheels and the other condition being the holding of the front wheels at a steering position beyond a predetermined angle
(c) calculating a friction coefficient of a road surface on which the vehicle is running on the basis of the data detected in said step (a) only when the proper steering situation is detected in said step (b); and
(d) calculating an equiphase steering angle of the rear wheels for steering the rear wheels in the same direction as the steering direction of the front wheels on the basis of the detected operating angle of the steering wheel and the friction coefficient of the road surface determined in said step (c) when the front wheels are steered, the equiphase steering angle for the rear wheels calculated in said step (d) being increased by a predetermined amount as the friction coefficient of the road surface calculated in said step (c) decreases.

12. The method according to claim 11, wherein in said step (d), an increasing amount of the equiphase steering angle of the rear wheels is decreased with increasing vehicle speed.

13. The method according to claim 12, wherein said step (d) includes preparing a map for reading the equiphase steering angle of the rear wheels, the map indicating an equiphase coefficient in accordance with the detected vehicle speed, and the equiphase coefficient increasing from zero as the vehicle speed increases from a predetermined speed and leveling off at a predetermined value, and wherein said step (d) further includes correcting the vehicle speed used for reading the equiphase coefficient so that the vehicle speed increases with the decrease in the calculated friction coefficient of the road surface, and multiplying the operating angle of the steering wheel by the equiphase coefficient read from the map in accordance with the corrected vehicle speed and then calculating the equiphase steering angle of the rear wheels from the multiplication result.

14. The method according to claim 11, wherein said step (d) includes a first process of calculating an opposite phase steering angle of the rear wheels in the direction opposite to the steering direction of the front wheel on the basis of an angular velocity obtained from the operating angle the steering wheel and the friction coefficient of the road surface, the opposite phase steering angle thus calculated being increased with the decrease in friction coefficient of the road surface, and a second process of finally calculating the steering angle of the rear wheels by adding the opposite phase steering angle to the equiphase steering angle of the rear wheels.

15. The method according to claim 14, wherein said step (d) further includes a third process executed between the first and second processes, the third process including setting the opposite phase steering angle at zero upon the calculated opposite phase steering angle failing to reach a predetermined value.

16. The method according to claim 14, wherein the first process is a process for preparing a map for reading the opposite phase steering angle of the rear wheels, the map indicating an opposite phase coefficient in accordance with the vehicle speed, the opposite phase coefficient being increased gradually and then decreased gradually as the vehicle speed increases, wherein the first process further includes a process of correcting the opposite phase coefficient so that it increases with the decrease in the calculated friction coefficient of the road surface, and a process of calculating the opposite phase steering angle of the rear wheels on the basis of the angular velocity of the steering wheel and the corrected opposite phase coefficient.

17. The method according to claim 14, wherein the method further includes a process of increasing the steering angle of the rear wheels by a predetermined amount in accordance with the angular velocity of the steering wheel, the predetermined amount being increased with the decrease in the calculated friction coefficient of the road surface.

18. A four-wheel steering system of a vehicle having front and rear wheels, comprising;
a steering wheel for steering the front wheels;
a hydraulic power steering unit disposed between the front wheels and the steering wheel;
first means for detecting an operating angle of the steering wheel;
second means for detecting a vehicle speed;
third means for detecting an operating pressure of the hydraulic power steering unit;
fourth means for determining an equiphase steering angle of the rear wheels to steer the rear wheels in the same direction as the steering direction of the front wheels, on the basis of the detected operating angle of the steering wheel when the front wheels are steered; and
rear steering means for steering the rear wheels in accordance with the equiphase steering angle of the rear wheels when the front wheels are steered, said rear steering means including fifth means for determining that a proper steering situation exists only when at least one of two conditions is satisfied during operation of the steering wheel, one condition being an increase in the steering angle of the front wheels and the other condition being the holding of the front wheels at a steering position beyond a predetermined angle, on the basis of the detected operating angle of the steering wheel, sixth means for calculating a friction coefficient of a road surface on which the vehicle is running on the basis of the detected operating angle of the steering wheel, the detected vehicle speed and the detected operating pressure only when at least one of the two conditions is satisfied, and seventh means for correcting the equiphase steering angle of the rear wheel so that it increases as the calculated friction coefficient of the road surface decreases.

* * * * *